United States Patent [19]

Glover et al.

[11] Patent Number: 4,464,123

[45] Date of Patent: Aug. 7, 1984

[54] ARM SIMULATOR FOR AN OSCILLOMETRIC BLOOD PRESSURE MONITOR

[75] Inventors: Wayne Glover, Odessa; Richard Medero, Lutz, both of Fla.

[73] Assignee: Critikon, Inc., Tampa, Fla.

[21] Appl. No.: 395,537

[22] Filed: Jul. 6, 1982

[51] Int. Cl.$^3$ ............................................. G09B 23/32
[52] U.S. Cl. ................................... 434/268; 128/681; 73/4 R
[58] Field of Search ................... 434/59, 262, 265–268, 434/307, 272, 323; 128/680–689, 713, 714, 715; 364/415–417; 73/1 B, 4 R

[56] References Cited

U.S. PATENT DOCUMENTS

| | | | |
|---|---|---|---|
| 3,376,660 | 4/1968 | McGinnis | 434/268 |
| 3,520,071 | 1/1968 | Abrahamson et al. | 434/265 |
| 3,689,748 | 9/1972 | Bothne | 73/4 R |
| 3,811,439 | 5/1974 | Brown | 128/681 |
| 3,868,844 | 3/1975 | Klein | 73/4 R |
| 4,271,843 | 6/1981 | Flynn | 128/681 |
| 4,301,512 | 11/1981 | Keith et al. | 364/416 |
| 4,360,029 | 11/1982 | Ramsey | 128/681 |

OTHER PUBLICATIONS

Darling, R. et al., "Quantitative Segmental Pulse Volume Recorder: A Clinical Tool", *Surgery*, Dec. 1972, vol. 72, No. 6, pp. 873–887.

*Primary Examiner*—Richard C. Pinkham
*Assistant Examiner*—MaryAnn Stoll
*Attorney, Agent, or Firm*—Audley A. Ciamporcero, Jr.

[57] ABSTRACT

A device for simulating the pressure readings obtained from the arm of a living subject whose blood pressure levels are being determined by an oscillometric blood pressure monitor, includes a pulse pressure chamber for generating pressure pulses at a rate equivalent to a preselected pulse rate. The input to the pressure chamber is attached to the pressure cuff of the monitor and the output is connected to the pressure transducer of the monitor. In order to balance the pressure across the chamber and to apply the full cuff pressure to the monitor transducer, a normally-open valve is connected across the pressure chamber. This valve, however, is closed when the chamber creates a pressure pulse so that the pulse is added to the applied cuff pressure at the monitor transducer. A processor generates electrical signals that control the amplitude of the pressure pulses created by the chamber, depending on preselected values for simulated systolic, mean arterial and diastolic pressures.

6 Claims, 7 Drawing Figures

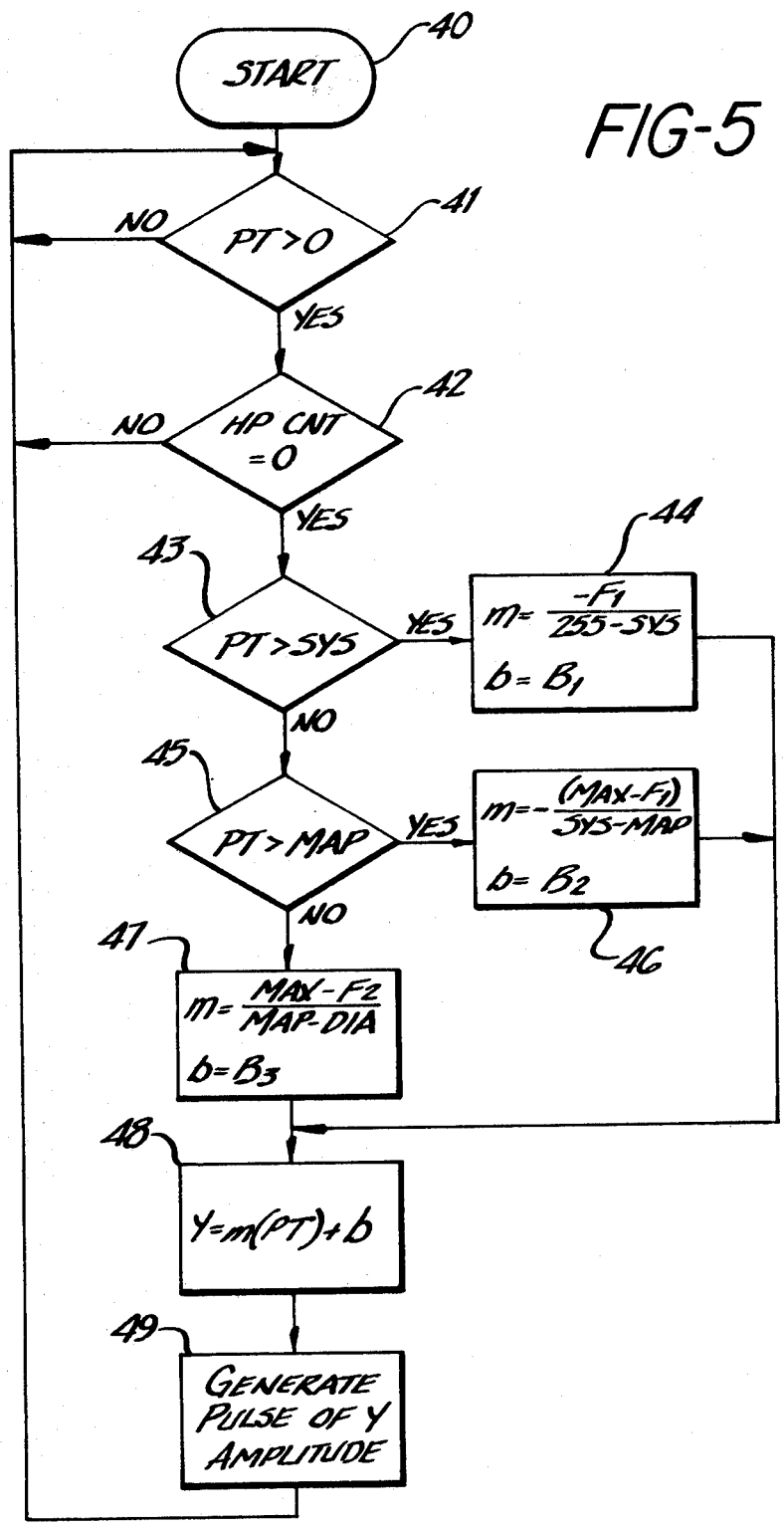

ARM SIMULATOR FOR AN OSCILLOMETRIC BLOOD PRESSURE MONITOR

FIELD OF THE INVENTION

This invention relates to the automated measurement of blood pressure by the oscillometric method and, more particularly, to devices for calibrating oscillometric blood pressure monitors.

BACKGROUND AND PRIOR ART

The measurement of the blood pressure of human beings is usually accomplished by applying a variable pressure through a pressure cuff to the brachial artery in the upper arm of the test subject. As the pressure is varied, the sound of the blood flow through the artery or the pressure pulses generated by the artery are usually measured and used as indications of various blood pressure values. These two techniques, known as the ausculatory and oscillometric methods, respectively, can both be automated.

With an automated ausculatory blood pressure monitor, a pump inflates the cuff such that the brachial artery, is occluded. Then the pressure is reduced in increments by the monitor and an audio transducer or microphone located on the arm of the subject adjacent the distal portion of the occluded artery converts the sound produced when blood flow is reestablished into electrical signals. These sound signals, known as "Korotkoff" or "K-sounds", are first detected when the cuff pressure is at a level known as the "systolic" pressure. The monitor continues to reduce the cuff pressure until these K-sounds disappear. The cuff pressure level where this occurs is known as the "diastolic" pressure. Once the systolic and diastolic pressures have been determined, the monitor deflates the cuff to zero pressure.

A typical automatic oscillometric blood pressure monitor also includes a pump which first inflates a pressure cuff around the upper arm of the subject to occlude the brachial cuff about the upper arm of the subject to occlude the brachial artery and then decreases the pressure in increments. However, instead of using an audio transducer on the arm, the oscillometric monitor uses a pressure transducer located in the monitor and connected to the cuff by a conduit. Even when the cuff has occluded the artery, the pumping of the heart of the subject causes the artery to flex or oscillate, resulting in pressure pulses that are received in the cuff and the transducer. As the pressure is decreased, the amplitude of the pulses increases to a maximum and then decreases again. The cuff pressure when the pulse amplitudes are at a maximum is known as "mean arterial pressure" (MAP). Also, the cuff pressures above and below MAP where the pulse amplitudes are predetermined fractions of the amplitude at MAP, represent the systolic and diastolic pressures, respectively.

The testing of automatic blood pressure monitors is typically very difficult because living subjects on which it may be tested may have different pressure levels at different times, and different subjects will have different pressure levels. Thus, the accuracy of the monitor with respect to its intended purpose can only be determined on a statistical basis by time consuming population studies. Since this is not possible on a production basis, typically only the electronics of the monitor are tested and a mercury manometer is used to test the accuracy with which the pressure transducer measures the cuff pressure. Then if the machine produces a correct reading for a single test subject known to have a stable blood pressure, it is assumed to be functioning properly. Obviously, the problem with this method of testing monitors is that there is no assurance that the monitor will operate to detect and measure pressure pulses in addition to the cuff pressure, or to measure blood pressures and pulse rates which are remote from those of the test subject. Also, a properly functioning monitor may be rejected if the test subject should have an unusual blood pressure level during the test.

It is known in the art to test automated auscultatory monitors by creating an artifical arm in the form of an inner cylinder filled with water in which sound waves approximating K-sounds are generated by a transducer. An outer layer of water in a flexible bag transmits the sound to the pressure cuff and microphone of the ausculatory monitor, and also simulates the compliance of a real arm. At present, however, there is no known method of simulating the arm of a test subject so that the pressure pulses of the oscillometric method can be generated for testing of a blood pressure monitor of that type.

DISCLOSURE OF THE INVENTION

The present invention is directed to apparatus suitable for simulating the arm of a living subject being tested for blood pressure readings by the oscillometric method. This object is accomplished by automatically inducing pressure pulses in the cuff of an oscillometric blood pressure monitor, which pulses occur at a predetermined, selectable rate and have amplitudes at various cuff pressures that indicate a selected value for systolic, distolic and mean arterial pressure.

In an illustrative embodiment of the invention, a device is provided for simulating the pressure pulsations typically monitored when blood pressure is measured by the oscillometric method. With this device, the performance of an oscillometric blood pressure monitor having an inflatable pressure cuff may be tested. The device has a pressure pulse chamber that includes an electrically actuated diaphragm adapted for generating pressure pulses related to an applied electrical signal. On one side of the diaphragm there is an input to the pressure chamber that is in pressure connection with the pressure cuff. In order to eliminate the need to vary the pressure pulses to compensate for applied cuff pressure levels, a controllable pressure valve is connected across the pressure chamber to balance the pressure across the diaphragm from the cuff. During a pressure pulse, however, the valve is closed so that the selected pulse amplitude is added to the cuff pressure, regardless of the cuff pressure. As a result, the output of the chamber is a pressure level equal to the sum of the pressure of the cuff and the pressure pulse created by the actuation of the diaphragm.

The signal which drives the diaphragm has a repetition rate that represents a selected pulse rate and an amplitude that varies with the applied pressure in the cuff of the blood pressure monitor so as to simulate the pressure pulsations of a subject having selected diastolic, mean arterial and systolic blood pressure values.

In a preferred embodiment, the amplitudes of the pressure pulses and rate are controlled by a microprocessor in response to selected pulse rate and pressure values.

BRIEF DESCRIPTION OF THE DRAWINGS

The foregoing and other features of the present invention will be more readily apparent from the following detailed description and drawings of an illustrative embodiment of the invention in which:

FIG. 5 is a flow chart describing the operation of the apparatus of FIG. 3;

DETAILED DESCRIPTION OF THE INVENTION

Figure 1:
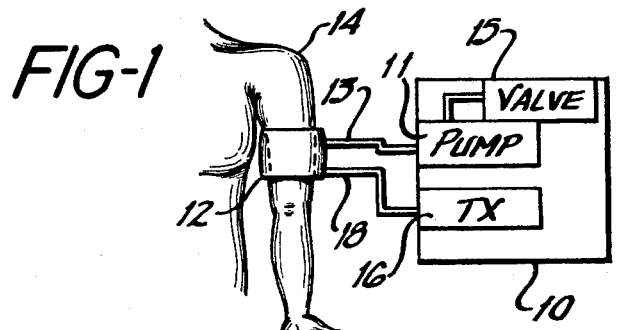
FIG. 1 illustrates the measurement of the blood pressure of a test subject with an oscillometric blood pressure monitor.
Figure 2:
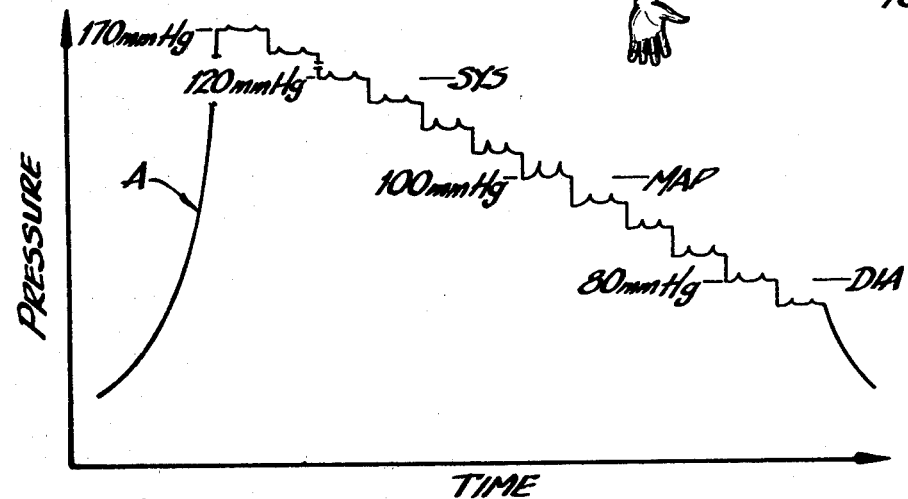
FIG. 2 is a graph of the pressure detected by the transducer of the blood pressure monitor of FIG. 1.

A conventional automatic oscillometric blood pressure monitor 10, such as that sold by Critikon Corp. of Tampa, Fla. as the Dinamap TM model 845, is shown in FIG. 1. In that figure, the monitor 10 is being used to test the blood pressure of a test subject. This is accomplished by inflating a pressure cuff 12 located about the upper arm 14 of the subject and detecting pressure pulsations induced in the cuff by the action of the subject's heart, while decreasing the cuff pressure from an initial high level. For this purpose, the monitor includes a pump 11 which is capable of automatically inflating the cuff via a tube 13 to a pressure high enough to occlude the brachial artery, e.g., about 170 mmHg, and a valve 15 capable of reducing this pressure in steps as shown in FIG. 2. Pressure pulses such as those shown at each step in FIG. 2, as well as the applied pressure, are delivered to the monitor over a conduit 18 and are detected by a transducer 16 located in the monitor. The transducer converts the pressure levels into an electrical signal which will have the same form as the pressure signal in FIG. 2.

In the monitor, the amplitudes of the pulses are detected and stored along with the corresponding values of the applied cuff pressure. This data is then reviewed to determined the applied pressure level at which the maximum pulse amplitudes occur. This pressure, which is shown as 100 mmHg in FIG. 2, is designated MAP. The applied cuff pressure above and below MAP at which the pulses are some fixed ratio of the amplitude at MAP are designated the systolic and diastolic pressures, respectively.

Usually, a monitor such as that in FIG. 1 is tested for accuracy by making sure the electronics and pressure transducer are functioning properly and then using the monitor to test one or more people whose blood pressure is known to be stable at a relatively fixed level. However, if only a few people are used for this test, there is no assurance that the monitor is capable of functioning over its complete range. Also, repeated testing tends to fatigue and irritate the test subjects, which may result in a change in their blood pressure that may be interpreted as a malfunction in the monitor.

Figure 3:
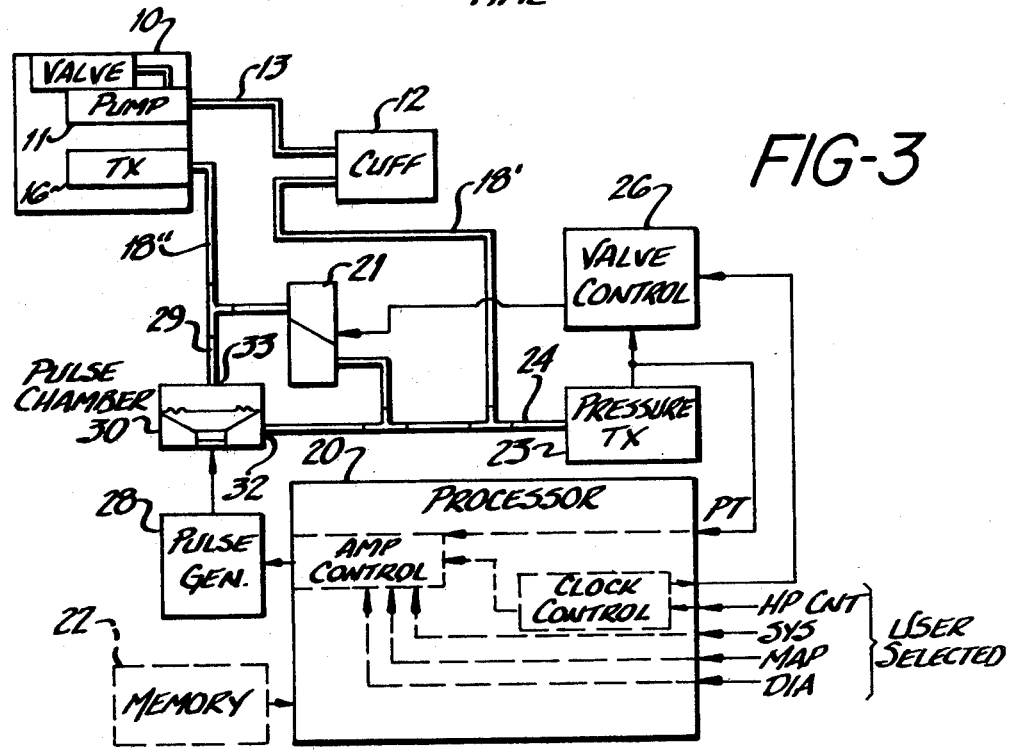
FIG. 3 illustrates apparatus according to the present invention for testing the oscillometric blood pressure monitor of FIG. 1.

In order to overcome the problems inherent in testing automated oscillometric blood pressure monitors, the simulator device shown in FIG. 3 is used. This device effectively simulates the arm of the test subject, but it can be set to give a wide variety of pulse rates and pressure levels. More particularly, the simulator device of FIG. 3 allows the pump of the monitor to inflate the cuff and, at the proper rate and level, it induces pressure pulsations in the cuff that duplicate those of a test subject's arm. This combination of the pressure level from the pump and the pulsations of the simulator are like that shown in FIG. 2 and are detected by transducer 16 of the monitor where they are processed to determined the preprogramed blood pressure levels.

When using the simulator, the pump of monitor 10 is connected to the pressure cuff 12 over conduit 13 in the same manner as when a living subject is measured. However, the return line or conduit 18 for applying the cuff pressure to the transducer of the monitor has the simulator device inserted in it for test purposes. A pulse rate, a systolic pressure and a diastolic pressure for the simulator are then selected by the user or operator. By means of a chart, the operator also selects a MAP level that is compatible with the selected values for systolic and diastolic pressure in a normal human being. It should be noted that any value of MAP between the selected values for systolic and diastolic pressure can be selected for the simulator, but the monitor may reject a MAP setting that is too far from normal levels. Of course, the selection of MAP may be preprogrammed into the simulator so that for any systolic and diastolic pressure, MAP is automatically selected. It is also possible to construct the simulator so that it will automatically select a variety of pulse rates and blood pressure levels so that the complete range of the monitor is tested without human intervention.

Within the simulator, the selected pressure values and pulse rates are directed to a processor, e.g., a microprocessor, that controls the operation of the simulator. The blood pressure monitor is operated in the usual manner while being tested by the simulator. It initially inflates the cuff 12 to a pressure of about 170 mmHg as shown in FIG. 2. This cuff pressure level is passed through the simulator to the transducer 16 of the monitor via conduits 18', 18" and a normally-open valve 21, which may be a Clippard EVO-3 valve. Since valve 21 is located across a pressure chamber 30, the cuff pressure is also applied to both sides of a diaphragm 36 (FIG. 6) located within the chamber. The cuff pressure is further applied to a pressure transducer 23 of the simulator over a conduit 24. As a result, an electrical signal related to the cuff pressure is generated and applied both to processor 20 and a control circuit 26 that operates valve 21.

The processor 20 causes an electrical pulse generator 28 to produce pulses at the selected pulse rate and with amplitudes that vary with the cuff pressure created by the monitor in such a way as to produce a signal simulating the selected blood pressure readings. These pulses drive an electrical coil 34 (FIG. 7) in the pressure chamber that causes diaphragm 36 to move and to produce a pressure pulse with an amplitude related to that of the electrical pulse applied to coil 34. At the same time the processor is activating the pulse generator, it is supplying a pulse signal to valve control circuit 26. This circuit in turn delivers a pulse to valve 21 so as to close it during the pressure pulse produced by pressure chamber 30. Since the pressure level at the output 33 of pressure chamber 30 is at the cuff pressure level and the output has been separated from the cuff by the closing of valve 21, the pressure chamber only needs to drive the volume of air in conduits 29 and 18'' leading from the chamber to the monitor. Consequently, the pressure applied to transducer 16 of the monitor will equal the pulse from the chamber plus the cuff pressure, thus producing a signal such as that in FIG. 2.

If there were a direct connection only between the cuff 12, transducer 16 and the output of pressure chamber 30, the pressure pulses would have to be created against the pressure force and volume of the entire cuff. Thus, the pulse amplitude would decrease at higher cuff pressure levels and it might not be possible to create pulses of reasonable amplitudes in the range of interest without using an excessively large pressure chamber and consuming large amounts of power. Also the amplitude of the signal from generator 28 would have to be made to vary not only with the level needed to produce the desired blood pressure levels, but also to compensate for the volume and level of the cuff pressure that chamber 30 would have to operate against. Further, the pressure differential across the diaphragm would require it to be of a heavy construction. However, by balancing the cuff pressure across the pressure chamber diaphragm 36 and using valve 21 to separate the output of the chamber from the cuff during a pulse generation: (i) the resulting pressure pulse is substantially independent of the applied cuff pressure, except as determined by the applied electrical signal, (ii) the cuff pressure at the input 32 of the chamber aids in pulse generation and (iii) the pulses can be produced with a smaller and more energy efficient pressure chamber.

Figure 4:
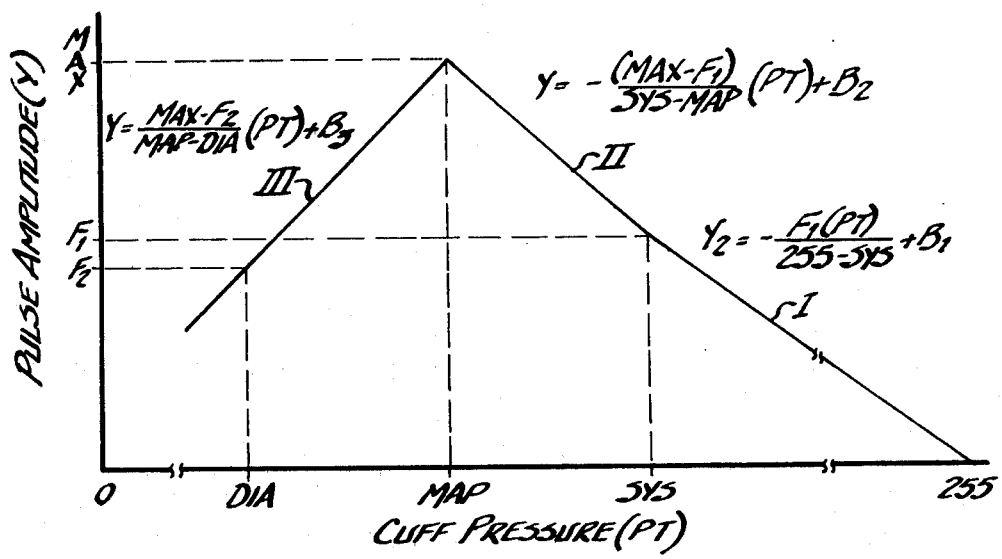
FIG. 4 is a graph of the equations for determining the pulse amplitudes produced by the apparatus of FIG. 3.

As previously stated, the amplitudes of the pressure pulses from a living test subject start at a low level and increase to a maximum level at MAP while the cuff pressure is reduced from its high initial level. In addition, the pulse amplitudes begin to decrease as the pressure level is decreased below MAP. The locus of such pulse peaks as shown in FIG. 4 is adequately represented by three straight line segments I, II and III. These segments have the usual line equation $Y = mx + b$, where Y is the amplitude, m is the slope, x is the cuff pressure (PT) and b is the Y axis intercept for each line, i.e. $B_1$, $B_2$ and $B_3$. The processor 20 has an input from pressure transducer 23 and in this way the processor obtains information as to the current cuff pressure (PT). Using this information along with the preset values for systolic pressure, diastolic pressure and MAP, the processor computes the required pulse amplitude according to the equations for the lines shown in FIG. 4. With this information an amplitude control section of the processor generates a series of digital signals that specify the shape and amplitude of the pulse. Thus, pulse generator 28 can be a digital-to-analog converter whose output is used to drive the electromagnetic coil 34 which operates diaphragm 36 to generate the pressure pulses. The larger the output of generator 28, the greater is the deflection of diaphragm 36 and the resulting pressure pulse.

The rate at which the pulses are generated is determined by the heart pulse rate selected by the user. This input is directed to a clock control portion of the processor which selects a division ratio of the basic processor clock from a heart pulse counter and uses it to time the operation of the amplitude control section. This timing signal from the heart pulse counter is also delivered to the valve control circuit 26 along with a signal from pressure transducer 23. In the valve control circuit, the timing signal is not only amplified to a level sufficient to drive the valve closed, it is logically combined with the signal from pressure transducer 23 so that valve 21 is automatically opened when there is a change in pressure of, e.g., 5 mmHg, indicating a controlled change in cuff pressure caused by the monitor. This is done to insure that the pressure across the diaphragm is balanced and that the pressure applied to the monitor is always at the level of the cuff pressure, even if a pulse is being produced. The valve control circuit, however, is set so that a change in pressure of less than 3 mmHg, for example, representing the output pulse from the pressure chamber, will not cause the valve to open.

A flow chart of the operation of processor 20 is shown in FIG. 5. In the situation in which processor 20 is a stored program microprocessor, as opposed to separate sequential logic blocks as generally indicated in FIG. 3, the flow chart of FIG. 5 would represent the program for that microprocessor stored in a memory circuit 22.

When operating, the processor first initializes its circuits as shown by function block 40 in FIG. 5. Then the processor checks in decision block 41 to see if the cuff pressure signal PT derived from transducer 23 is above 10 mmHg. If it is not, the processor continues to loop until this condition changes. As soon as the cuff pressure increases above 10 mmHg, indicating that the pressure monitor has begun to take a reading by inflating the cuff, the processor moves on to decision block 42 where it checks to see if a heart rate signal, HPCNT, has been set. If no heart rate level has been set, the processor returns to its initial state. If it has been set, the processor moves to decision block or state 43 where it determines if the cuff pressure is above systolic levels. Suitable programming can be included to assure that this decision is not made until the cuff pressure has reached its maximum level and has begun to decrease, i.e. a delay may be added to the decision level to assure that the decision in block 43 is not made during inflation of the cuff, shown as section A of the curve in FIG. 2.

When the cuff pressure is above systolic, the processor generates pulse information for pulses whose amplitudes are related to the line equation identified by I in FIG. 4. Thus, as the pressure decreases in the range above systolic pressure, the pulse amplitudes increase in value. The curve I in FIG. 4 is selected to be zero at a pulse level of 255, but this level was picked arbitrarily based on the capacity of storage elements used in the processor. The amplitude of the curve at systolic pressure is some preselected fraction $F_1$ of the maximum at MAP. Thus, in the range of pressures above systolic, the value for the slope of the line, i.e. m, as well as the zero axis crossing b are set in logic block 44 and these values are substituted in the line equation in decision block 48. The processor then converts the line equation into the generation of pulses having an amplitude according to the line equation in logic block 49, after which it loops through the blocks 41–44, 48 and 49 again until the applied cuff pressure is below systolic.

When the cuff pressure is below systolic, the processor moves from decision block 43 to decision block 45, which is operative to direct the processor to logic block 46 when the applied pressure is between systolic pressure and MAP. The pulse amplitudes in this region are represented by the line equation II in FIG. 4. The values for the equation of this line, i.e., the slope m and zero crossing $B_1$, are generated in block 46 and are applied to equation block 48 which in turn causes pulse generator block 49 to generate another series of pulses which increase a larger amount for each pressure decrement, than the pulses for pressures above systolic. This process continues until the cuff pressure is equivalent to MAP. At this point, the pulse amplitudes begin to decrease according to equation III in FIG. 4. The values for this equation are derived from logic block 47 in the flow chart. Thus, by knowing the selected systolic, MAP and diastolic pressures, the processor is able to duplicate the variation in pulse amplitudes of a living test subject.

Figure 7:
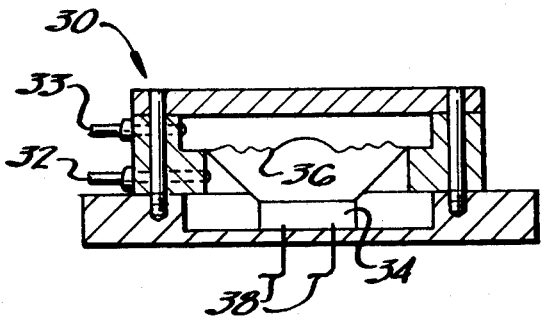
FIG. 7 is a sectional view along line 7—7 of the pulse pressure chamber of FIG. 6.
Figure 6:
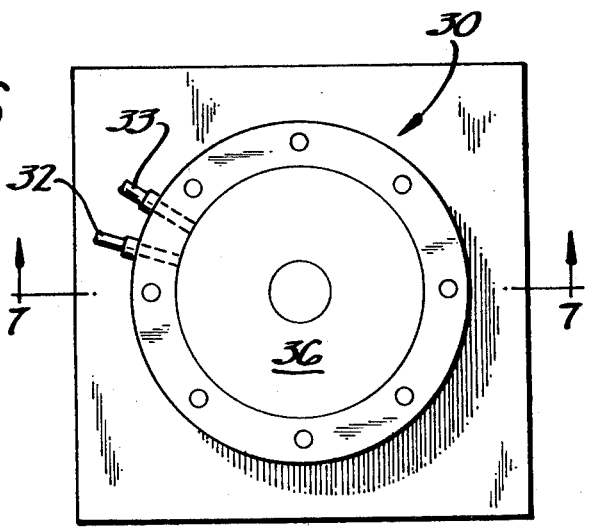
FIG. 6 is an enlarged plan view of the pulse pressure chamber of FIG. 3.

The details of the pressure chamber itself are shown in FIGS. 6 and 7. In these figures, it can be seen that the pressure chamber is a generally cylindrical housing about three inches in diameter and made of any suitable material, for example clear plastic. Located in the middle of the housing is a diaphragm 36 which typically can be a conventional audio speaker with a driving coil 34. For operation in the pressure chamber, an audio speaker that has a large magnet and a small cone support with a round shape, should be selected. The speaker should have its frame removed and all of the backing, except for the spider cloth net. Then, a latex coating should be applied to the spider.

The output of generator 28 is connected to the driving coil 34 of the speaker via leads 38, thereby causing the diaphragm 36 to flex in response to signals from the generator. This flexing of the diaphragm produces pressure pulses at the output 33 of the pressure chamber. As previously explained, the input 32 to the pressure chamber has the cuff pressure applied to it. Thus, the chamber, under the control of processor 20 and with the assistance of valve 21, is capable of producing pressure pulsations similar to those produced by the arm of a subject under going a test for blood pressure readings according to the oscillometric method.

While the present invention has been particularly shown and described with reference to a preferred embodiment thereof, it will be understood by those skilled in the art that various changes in form and details may be made therein without departing from the spirit and scope of the invention.

We claim:

1. A simulator device for simulating the pressure pulsations from a subject whose blood pressure is being determined by an oscillometric blood pressure monitor with an inflatable pressure cuff, comprising:

a. pressure chamber means with an input and an output for creating a pressure pulse at its output related to an applied electrical signal, the input being in pressure communication with the pressure cuff, and the output being in pressure communication with the monitor;

b. means for generating the applied electrical signal in the form of a series of pulses occurring at a preselected rate, the amplitudes of said pulses being adjusted in response to the pressure in the pressure cuff to simulate the pressure pulses of a test subject with selected blood pressure values;

c. a controllable pressure valve connected between the input and output of the pressure chamber, said valve normally being open; and d. means for closing said valve for a period substantially equal to the period of said pressure pulse, so that the total pressure at the output of the pressure chamber means is the sum of the pressure pulse and the pressure applied from the pressure cuff;

e. wherein said pressure chamber means comprises
      (i) a hollow housing with an input port coupled to the input of said pressure chamber and an output port coupled to the output of said pressure chamber,
      (ii) a diaphragm dividing the interior of said housing between said input port and said output port, and
      (iii) means for causing movement of said diaphragm in response to an electrical signal, the amplitude, direction and frequency of the movement being related to the amplitude, polarity and frequency of the electrical signal.

2. A simulator device as claimed in claim 1 wherein said means for causing movement includes an electromagnet.

3. A simulator device as claimed in claims 2 or 1 wherein the means for generating the applied electrical signal varies the peak amplitude of the pulses in relation to selected values for simulated systolic, mean arterial and diastolic pressures.

4. A simulator device as claimed in claim 3 wherein the means for generating the applied electrical signal causes the peak amplitudes of the pulses to vary such that:

when the applied cuff pressure is between the selected values for diastolic and means arterial pressure, the peak amplitudes of the pulses are linearly related to one another in the range between a maximum pulse amplitude at means arterial pressure and a first fraction of the maximum pulse amplitude at the diastolic pressure;

when the applied cuff pressure is between the selected values for mean arterial pressure and systolic pressure, the peak amplitudes of the pulses are linearly related to one another in the range between a maximum pulse amplitude at mean arterial pressure and a second fraction of the maximum pulse amplitude at the systolic pressure; and when the applied cuff pressure is between the selected value for systolic pressure and a certain fixed pressure level significantly exceeding systolic pressure, the peak amplitudes of the pulses are linearly related to one another in the range between a pulse amplitude equal to the second fraction of the maximum at the systolic pressure and a pulse amplitude of zero at the fixed pressure level.

5. A simulator device as claimed in claim 4, wherein the means for generating the applied electrical signal includes a microprocessor programmed to calculate the linear relationships and to control the pulse amplitudes in response to those calcalutions.

6. A simulator device as claimed in claim 1 wherein said means for controlling the valve includes means for assuring that the valve is open whenever there is a change in cuff pressure above a certain value, even during the generation of a pulse.

* * * * *

UNITED STATES PATENT AND TRADEMARK OFFICE
CERTIFICATE OF CORRECTION

PATENT NO. : 4,464,123
DATED : August 7, 1984
INVENTOR(S) : Wayne Glover, Richard Medero It is certified that error appears in the above—identified patent and that said Letters Patent is hereby corrected as shown below:

Col. 8, line 35 "means" should be--mean;

col. 8, line 38 "means" should be--mean--;

col. 8, line 60 "calcalutions" should be--calculations--.

Signed and Sealed this

Fourteenth Day of May 1985

[SEAL]

Attest:

DONALD J. QUIGG

Attesting Officer — Acting Commissioner of Patents and Trademarks